United States Patent [19]

Fainzilberg et al.

[11] 4,183,241

[45] Jan. 15, 1980

[54] DIGITAL DEVICE FOR CHECKING CARBON EQUIVALENT IN MOLTEN IRON

[75] Inventors: Leonid S. Fainzilberg; Leonid S. Zhitetsky, both of Kiev, U.S.S.R.

[73] Assignee: Institut Kibernetiki Akademii Nauk Ukrainskoi SSR, Kiev, U.S.S.R.

[21] Appl. No.: 916,366

[22] Filed: Jun. 16, 1978

[30] Foreign Application Priority Data

Jun. 20, 1977 [SU] U.S.S.R. .................... 2500554[1]

[51] Int. Cl.$^2$ ............... G06F 15/20; G01N 25/02
[52] U.S. Cl. ........................................ 73/17 R
[58] Field of Search ............ 73/17 R; 75/130 R; 364/472, 497, 499, 557

[56] References Cited

U.S. PATENT DOCUMENTS

| 3,891,834 | 6/1975 | Warsinski | 73/17 |
| 4,088,974 | 5/1978 | Zhitetsky et al. | 73/17 |

*Primary Examiner*—Herbert Goldstein
*Attorney, Agent, or Firm*—Haseltine, Lake & Waters

[57] ABSTRACT

The device comprises a converter for converting the actual temperature of metal to a digital pulse code and a clock pulse generator which are connected through their outputs to a synchronization unit. A synchronized clock pulse output of the synchronization unit is connected to a count input of a time interval counter; synchronized code pulse outputs of the synchronization unit are connected to add and subtract inputs of a reversible counter and a threshold counter having overflow outputs connected to reset inputs of the time interval counter. The device also comprises a code selection unit with its inputs connected to digit outputs of the reversible counter which is provided with a count suppression input. The device further includes a flip-flop, a NOT element, and two gates with their inputs connected to the overflow output of the time interval counter, and their outputs connected to set and reset inputs of the flip-flop. An output of the flip-flop is connected to the count suppression input of the reversible counter, and an output of the code selection unit is connected to the control input of the first gate and, through the NOT element, to the control input of the second gate.

1 Claim, 9 Drawing Figures

DIGITAL DEVICE FOR CHECKING CARBON EQUIVALENT IN MOLTEN IRON

FIELD OF THE INVENTION

The present invention relates to apparatus for the physicochemical analysis of metals and alloys and, more particularly, to digital devices for checking the carbon equivalent in molten iron.

The invention is applicable to ferrous metallurgy and machine building for automatically checking the carbon equivalent in molten iron during melting processes.

BACKGROUND OF THE INVENTION

There is widely known a thermographic method for analyzing the composition of a metal, according to which the impurities content in the metal is determined with reference to temperature arrests on the cooling curve of a sample of molten metal. This method makes it possible to check the carbon equivalent in molten iron with reference to the crystallization onset temperature (the liquidus temperature).

Known in the art is a digital device for automatically checking the carbon content in a molten metal with reference to the liquidus temperature (cf. U.K. Pat. No. 1,477,564). This device is applicable for determining and displaying in a digital form the carbon equivalent in molten iron with reference to the liquidus temperature, which is found as follows:

$$C_E = F(T_1), \quad (1)$$

where $C_E$ is the carbon equivalent;
$T_1$ is the liquidus temperature; and
F is an operator defining a relation between the above values.

The device under review comprises a converter, for converting the actual temperature of the metal to a digital pulse code, which is fed at its input with a signal carrying information on the actual temperature of the metal and whose code pulse outputs, corresponding to positive and negative increments of temperature, are connected to inputs of a synchronization unit intended for time distribution of code and clock pulses. The device further comprises a clock pulse generator whose output is connected to the synchronization unit. The synchronized clock pulse output of the synchronization unit is connected to the count input of a time interval counter; the synchronized code pulse outputs of the synchronization unit are connected to add and subtract inputs of a reversible counter and a threshold counter. The threshold counter is constructed so that after the arrival of a number of pulses, corresponding to a certain value $\pm \epsilon$, at any of its inputs, there is formed a pulse at one of its overflow outputs. The value $\epsilon_o$ is the threshold of non-sensitivity to the temperature changes in the metal during crystallization. The overflow outputs of the threshold counter are connected to the set inputs of the time interval counter which is a non-reversible pulse counter, and is constructed so that a pulse is formed at its overflow output only on condition that a time interval between its successive settings is in excess of a predetermined threshold $\tau_o$. The overflow output of the time interval counter is connected to the control input of a register having an information input connected to the digit outputs of the reversible counter. The register is connected through its output to a functional code converter, which converts, in accordance with the operator F, a parallel code applied to its information input from the reversible counter. The output of the functional code converter is connected to a digital display unit.

The device operates as follows. While a sample of a metal is cooling down, code pulses from the converter for converting the actual temperature of a metal to a digital pulse code, are applied through the synchronization unit to the inputs of the threshold counter and to the add and subtract inputs of the reversible counter which simultaneously generates the parallel code corresponding to the actual temperature of the metal. Each time when the temperature increment equals $\pm \epsilon_o$, a signal is formed at an overflow output of the threshold counter. These signals arrive at the reset inputs of the time interval counter. The sychronized clock pulses are applied to the count input of the time interval counter. After each setting of the time interval counter, the counter starts time measurement, i.e. counting synchronized clock pulses. After a certain period of time $\tau_o$ has elapsed since the last setting of the time interval counter, there is formed a pulse at its overflow output. This pulse is formed only on condition that during said period of time $\tau_o$ the next pulse is not applied to the reset inputs of the time interval counter. Arriving at the control input of the register, the pulse from the overflow output of the time interval counter delivers the content of the reversible counter to the register, the content being the code corresponding to the liquidus temperature $T_1$ of the metal. With the aid of the functional code converter, the liquidus temperature code is converted to a code corresponding to the carbon equivalent. The digital display unit displays the result in a digital form.

Thus, the above device automatically checks the carbon equivalent in a molten iron in compliance with the relationship (I).

More accurate results can be obtained if said value is determined by the difference between the liquidus temperature $T_1$ and the solidus temperature $T_s$. However, the known device does not provide for automatic checking of the temperature $T_s$ during the cooling of a sample of molten iron, and, therefore, does not ensure the required accuracy in determining the carbon equivalent.

SUMMARY OF THE INVENTION

The principal object of this invention is to provide, on the basis of simple computing elements and units, a digital device, for checking the carbon equivalent in molten iron, which ensures a higher accuracy in determining the carbon equivalent by way of automatically detecting the liquidus and solidus temperature arrests during the cooling of a sample of a metal, and determining the carbon equivalent in molten iron by the difference between the temperatures at which said temperature arrests occur.

This and other objects of the invention are accomplished insofar that a digital device for checking the carbon equivalent in molten iron, comprising a converter for converting theactual temperature of the metal to a digital pulse code, having code pulse outputs connected to a first input and a second input of a synchronization unit having a third input connected to an output of a clock pulse generator, a synchronized clock pulse output connected to a count input of a time interval counter for selecting time intervals during which predetermined temperature increments of metal occur, synchronized code pulse outputs connected to respective add and subtract inputs of a reversible counter and a threshold counter having overflow outputs connected to reset inputs of the time interval counter, further includes, according to the invention, a code selection unit having inputs connected to digit outputs of the reversible counter which is provided with a count suppression input, a flip-flop, a NOT element, and two gates having inputs connected to the overflow output of the time interval counter, and outputs connected to set and reset inputs of the flip-flop having an output connected to the count suppression input of the reversible counter, an output of the code selection unit being connected to a control input of the first gate and, through the NOT element, to a control input of the second gate.

The device according to the invention makes it possible to automatically detect the liquidus and solidus temperature arrests during the cooling of a sample of iron and to determine the carbon equivalent in molten iron by the difference between the temperatures whereat these arrests occur. This ensures a higher accuracy in checking the carbon equivalent.

The above and other objects of the invention will become more apparent from the following detailed description of preferred embodiments thereof, taken in conjunction with the accompanying drawings.

DETAILED DESCRIPTION OF THE INVENTION

Figure 1:
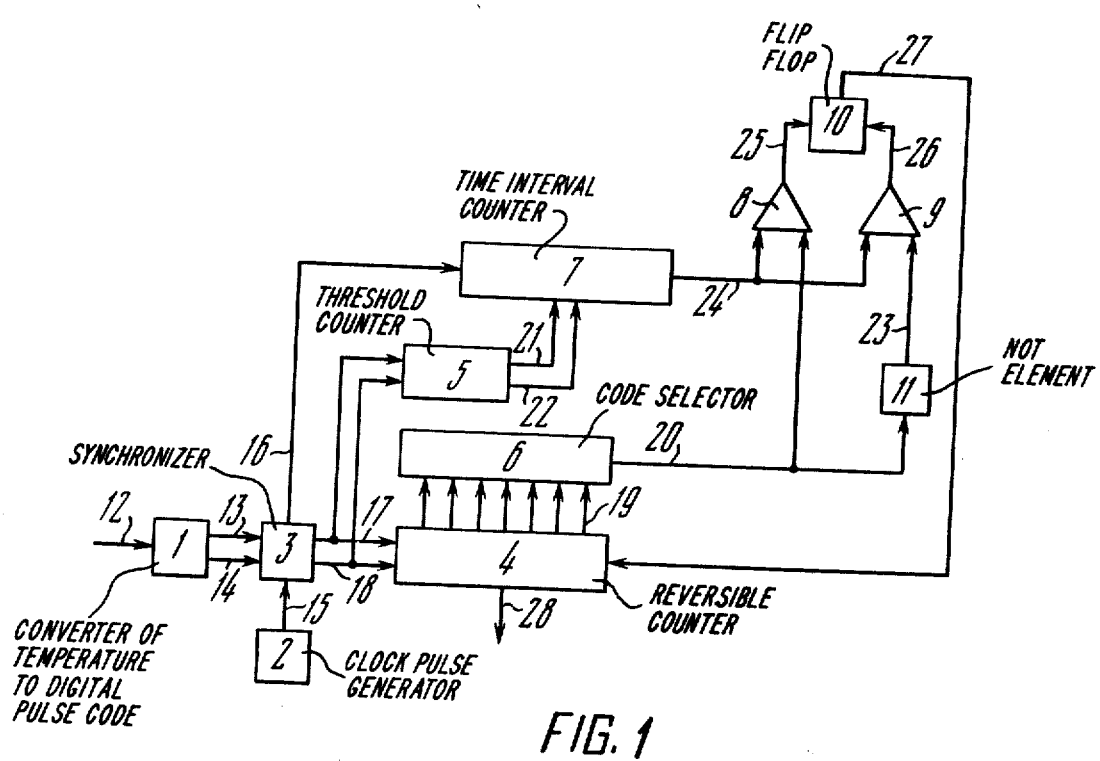
FIG. 1 is a block diagram of a digital device for checking the carbon equivalent in molten iron, according to the invention.

The proposed device for checking the carbon equivalent in molten iron, as shown in FIG. 1, comprises a converter 1 for converting the actual temperature of the metal to a digital pulse code, a clock pulse generator 2, a synchronization unit 3, a reversible counter 4, a threshold counter 5, a code selection unit 6, a time interval counter 7, gates 8 and 9, a flip-flop 10, and a NOT element 11. An input 12 of the converter 1 is intended to receive a signal carrying information regarding the actual molten iron temperature. Outputs 13 and 14 of the converter 1 for code pulses corresponding to positive and negative increments of temperature are connected to the inputs of the synchronization unit 3. An output 15 of the clock pulse generator 2 is connected to another input of the unit 3. A synchronized clock pulse output 16 of the synchronization unit 3 is connected to a count input of the time interval counter 7, and synchronized code pulse outputs 17 and 18 of the synchronization unit 3 are connected to add and subtract inputs of the reversible counter 4 and the threshold counter 5, the output 17 connected to the subtract inputs, and the output 18 connected to the add inputs of said counters. Digit outputs 19 of the reversible counter 4 are connected to inputs of the code selection unit 6. An output 20 of the code selection unit 6 is connected to a control input of the gate 8 and to an input of the NOT element 11. Overflow outputs 21 and 22 of the threshold counter 5 are connected to reset inputs of the time interval counter 7. An output 23 of the NOT element 11 is connected to a control input of the gate 9. Inputs of the gates 8 and 9 are connected to an overflow output 24 of the time interval counter 7. Outputs 25 and 26 of the gates 8 and 9 are connected to a set input and a reset input, respectively, of the flip-flop 10. The set output 27 of the flip-flop 10 is connected to a count suppression input of the reversible counter 4. With its information output 28, the reversible counter 4 can be connected to a digital display unit, a numeric printer or any other data display or recording means (not shown).

Figure 2:
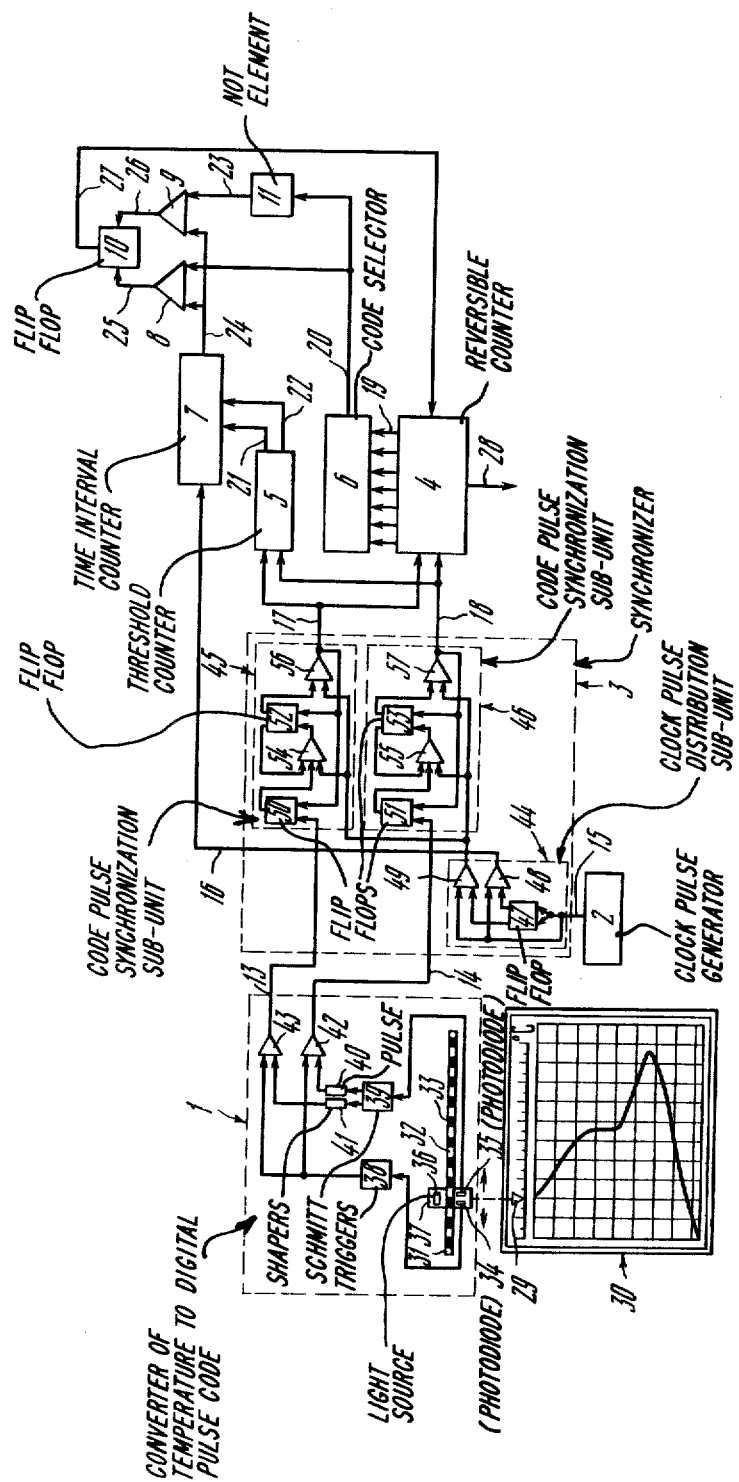
FIG. 2 is a logic diagram of an alternative embodiment of the digital device for checking the carbon equivalent in molten iron, according to the invention.

FIG. 2 shows an alternative embodiment of the device according to the invention. The input 12 of the converter 1 is mechanically coupled to a rheostat slide 29 of an automatic potentiometer 30, whereto there is continuously applied a signal from a temperature sensor (not shown).

The converter 1 comprises a measuring scale 31 with alternating transparent marks 32 and non-transparent marks 33 of an equal width. The number of the marks determines the resolving power of the converter 1. The converter 1 further comprises two photodiodes 34 and 35 and a light source 36 which are mounted on a holder 37. The photodiodes 34 and 35 are spaced at a distance equal to half the width of the marks 32 and 33.

The holder 37 of the converter 1 is mechanically coupled to the rheostat slide 29 of the automatic potentiometer 30.

In addition, the converter 1 includes two Schmitt triggers 38 and 39, two pulse shapers 40 and 41 forming pulses on the positive front edge of the signal which is applied from the outputs of the Schmitt trigger 39, as well as two gates 42 and 43 for selecting code pulses corresponding to positive and negative temperature increments on the cooling curve.

An input of the Schmitt trigger 38 is connected to an output of the photodiode 34, whereas an input of the Schmitt trigger 39 is connected to an output of the photodiode 35. A reset output of the Schmitt trigger 38 is connected to control inputs of the gates 42 and 43. A set output of the Schmitt trigger 39 is connected to an input of the pulse shaper 40, while a reset output of the Schmitt trigger 39 is connected to an input of the pulse shaper 41.

The output of the pulse shaper 40 is connected to the pulse input of the gate 42, whereas an output of the pulse shaper 41 is connected to a pulse input of the gate 43.

At the outputs of the gates 42 and 43 there are formed code pulses of the converter 1, corresponding to positive and negative temperature increments on the cooling curve.

Other versions of said converter 1 are also possible.

The synchronization unit 3 has a clock pulse distribution sub-unit 44 and code pulse synchronization sub-units 45 and 46. The clock pulse distribution sub-unit 44 comprises a flip-flop 47 for distributing clock pulses, a gate 48 for forming synchronized clock pulses, and a gate 49 for forming synchronizing clock pulses. The control inputs of the gates 48 and 49 are connected to outputs of the flip-flop 47. The pulse inputs of the gates 48 and 49 are combined and connected to the count input of the flip-flop 47. Said pulse inputs are the input of the synchronization unit 3, whereto there are applied pulses from the clock pulse generator 2. An output of the gate 48 is the synchronized clock pulse output 16 of the synchronization unit 3. The code pulse synchronization sub-units 45 and 46 comprise flip-flops 50 and 51 for storing code pulses, buffer flip-flops 52 and 53, AND gates 54 and 55, and gates 56 and 57 for forming synchronized code pulses. A set input of the flip-flop 50 is the input of the synchronization unit 3 for code pulses corresponding to a positive increment of temperature on the cooling curve. A set input of the flip-flop 51 is the input 14 of the synchronization unit 3 for code pulses corresponding to a negative increment of temperature on the cooling curve. Inputs of the AND gate 54 are connected to an input of the flip-flop 50 and to a reset output of the flip-flop 52.

The inputs of the AND gate 55 are connected to the set output of the flip-flop 51 and to the reset output of the flip-flop 53. The third input of each of the AND gates 54 and 55 is connected to the output of the gate 49 which forms synchronizing clock pulses of the distribution sub-unit 44. The output of the gate 49 is connected to one input of the gate 54 of the synchronization sub-unit 45 and to an input of the gate 57 of the synchronization sub-unit 46.

Other inputs of each of the gates 56 and 57 are respectively connected to the set outputs of the flip-flops 52 and 53. An output of the AND gate 54 is connected to the set input of the flip-flop 52, and the output of the AND gate 55 is connected to the set input of the flip-flop 53. An output of the gate 56 is connected to the reset inputs of the flip-flops 50 and 52, and is the output 17 of the synchronization unit 3 for synchronized code pulses corresponding to a positive increment of temperature on the cooling curve.

An output of the gate 57 is connected to the reset inputs of the flip-flops 51 and 53 and is the output 18 of the synchronization unit 3 for synchronized code pulses corresponding to a negative increment of temperature on the cooling curve.

The threshold counter 5 is constructed so that at its overflow outputs there are formed pulses each time the number of code pulses applied to its input is in excess of a predetermined value $\epsilon_o$.

The time interval counter 7 is constructed so that at its overflow outputs there is formed a pulse only if the time interval between the two successive pulses applied to its initial setting inputs is in excess of a predetermined threshold $\tau_o$.

The code selection unit 6 may be constructed as a decoder so that at its output 20 there is formed an enable potential provided the content of the reversible counter 4 differs from a certain value $C_o$ by a value which does not exceed $\epsilon_o$. Otherwise, at the output 20 of the code selection unit 6 there is formed a disable potential.

The digital device for checking carbon equivalent in molten iron operates as follows.

Prior to the start of each checking cycle, a code corresponding to a certain value $C_o$ is entered into the reversible counter 4 by means of a set button (not shown) and the flip-flop 10 is reset. The disable potential from the set output 27 of the flip-flop 10 is blocking the reversible counter 4, and at the output 20 of the code selection unit 6 there is formed an enable potential.

The temperature of a sample of molten iron is detected, while it is cooling down, using a conventional temperature sensor, and the cooling curve is recorded with the aid of a potentiometer 30, the signal carrying information on the temperature of metal being converted by the converter 1, to a digital pulse code.

Figure 3:
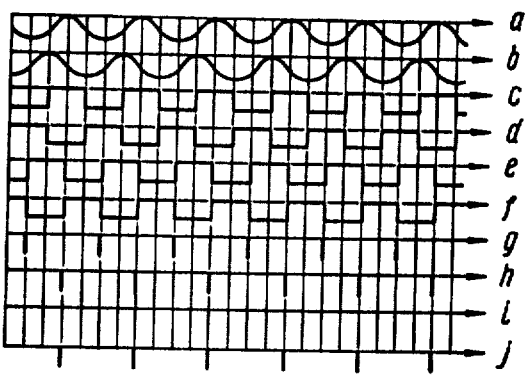
FIG. 3 shows time plots illustrating the operation of a converter for converting the actual temperature of the metal to a digital pulse code, according to the invention, in case of a positive increment of temperature.
Figure 4:
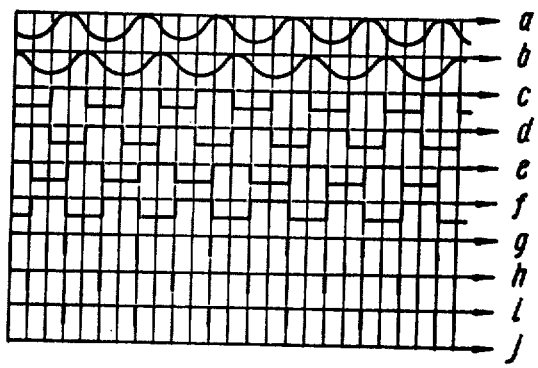
FIG. 4 shows the time plots for the case of a negative increment of temperature.

The operating principle of the converter 1 shown in FIG. 2 is illustrated by the time plots of FIG. 3 and FIG. 4.

The movement of the rheostat slide 29 of the automatic potentiometer 30 is parallel to that of the holder 37 of the converter 1. The luminous flux of the light source 36, which is incident on the photodiodes 34 and 35, is modulated by the marks 32 and 33 on the measuring scale 31. From the photodiodes 34 and 35, signals are applied to the inputs of the Schmitt triggers 38 and 39, respectively.

As the rheostat slide 29 moves from left to right, the signal (FIG. 3a) of the photodiode 34 (FIG. 2) is a quarter of a period behind the signal (FIG. 3b) of the photodiode 35 (FIG. 2). In this case the signal (FIG. 3c) at the set output and the signal (FIG. 3d) at the reset output of the Schmitt trigger 38 (FIG. 2) are a quarter of a period behind the signal (FIG. 3e) at the set output and the signal (FIG. 3f) at the reset output of the Schmitt trigger 39 (FIG. 2), respectively.

The pulse shaper 40 forms pulses (FIG. 3g) on the positive front edge of the signal (FIG. 3e) which is applied from the set output of the Schmitt trigger 39 (FIG. 2). The pulse shaper 41 forms pulses (FIG. 3h) on the positive front edge of the signal (FIG. 3f) which is applied from the reset output of the Schmitt trigger 38 (FIG. 2).

Pulses (FIG. 3g) from the output of the pulse shaper 40 (FIG. 2) are applied to the pulse input of the gate 42. Pulses (FIG. 3h) from the output of the pulse shaper 41 (FIG. 2) are applied to the pulse input of the gate 43. Signals (FIG. 3d) from the reset output of the Schmitt trigger 38 (FIG. 2) are applied to the control inputs of the gate 42 and the gate 43. The time plot (FIG. 3) shows that at a moment when signals are applied to the pulse input of the gate 42 (FIG. 2), said gate 42 is not conducting because to its control input there is applied a disable signal from the reset output of the Schmitt trigger 38. At moments when signals are applied to the pulse input of the gate 43, said gate 43 is conducting because to its control input there is applied an enable signal from the reset output of the Schmitt trigger 38.

As the rheostat slide 29 (FIG. 2) moves from left to right, no signals are formed (FIG. 3c) at the output of the gate 42 (FIG. 2). Signals (FIG. 3j) at the output of the gate 43 (FIG. 2) are code pulses of the converter 1, corresponding to a positive increment of temperature on the cooling curve.

As the rheostat slide 29 (FIG. 2) moves from right to left, the signal (FIG. 4a) of the photodiode 34 (FIG. 2) is a quarter of a period ahead of the signal (FIG. 4b) of the photodiode 35 (FIG. 2). As a result, at moments when pulses (FIG. 4g) from the pulse shaper 40 (FIG. 2) are applied to the pulse input of the gate 42, enable signals (FIG. 4d) are applied to the control input of the gate 42 from the reset output of the Schmitt trigger 38 (FIG. 2). At moments when pulses (FIG. 4h) of the pulse shaper 41 (FIG. 2) are applied to the pulse input of the gate 43, disable signals (FIG. 4d) are applied to the control input of the gate 43 from the reset output of the Schmitt trigger 38 (FIG. 2).

Hence, as the rheostat slide 29 (FIG. 2) moves from right to left, no signals are formed (FIG. 4f) at the output of the gate 43 (FIG. 2). Signals (FIG. 4l) at the output of the gate 42 (FIG. 2) are code pulses of the converter 1, corresponding to a negative increment of temperature on the cooling curve.

Depending on the sign of temperature increment, code pulses are applied from the outputs 13 and 14 of the converter 1 to the inputs of the synchronization unit 3 which is also fed with clock pulses from the clock pulse generator 2.

Figure 5:
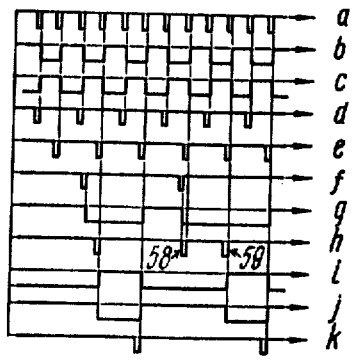
FIG. 5 shows time plots illustrating the operation of the synchronization unit according to the invention.

The operating principle of the synchronization unit 3 shown in FIG. 2 is illustrated by the time plots of FIG. 5.

As clock pulses (FIG. 5a) are applied from the generator 2 to the count input of the flip-flop 47 of the clock pulse distribution sub-unit 44, said flip-flop successively changes its state. Signals from the set (FIG. 5c) and reset (FIG. 5b) outputs of the flip-flop 47 are respectively applied to the control inputs of the gates 48 and 49. Applied to the pulse inputs of these gates are clock pulses (FIG. 5a) from the generator 2. As a result, at the outputs of said gates there are formed two pulse trains, shifted in time relative to each other. At the output of the gate 48 there are formed synchronized clock pulses (FIG. 5d), and at the output of the gate 49 there are formed synchronizing clock pulses (FIG. 5e).

The repetition frequency $f_1$ of the synchronized clock pulses is equal to the repetition frequency $f_2$ of the synchronizing clock pulses and amounts to $$f_1 = f_2 = \tfrac{1}{2} f_0 \tag{2}$$

where $f_0$ is the repetition frequency of pulses arriving from the output 15 of the clock pulse generator 2.

The synchronized clock pulses are applied to the output 16 of the synchronization unit 3.

The synchronizing clock pulses are applied to the inputs of the AND gate 54 and the gate 56 of the synchronization sub-unit 45, as well as to the inputs of the AND gate 55 and the gate 57 of the synchronization sub-unit 46. In the initial state, all the flip-flops 50, 51, 52 and 53 are zeroed by a button (not shown). As a code pulse (FIG. 5g) corresponding to a positive increment of temperature on the cooling curve is applied from the output of the converter 1, the flip-flop 50 (FIG. 3) is set (FIG. 5h). After a change in the state of the flip-flop 50, at the moment of the arrival of the next synchronizing clock pulse, at the output of the AND gate 54 there is formed a pulse (FIG. 5i) which sets the buffer flip-flop 52 (FIG. 5k); as a result, the gate 56 is driven into conduction.

At the moment of the arrival of the next synchronizing clock pulse (FIG. 5e,j), at the output of the gate 56 there is formed a synchronized code pulse (FIG. 5l) corresponding to a positive increment of temperature. This pulse is applied to the output 17 of the synchronization unit 3, and also to the inputs of the flip-flops 50 and 52. The signal (FIG. 5j) applied from the reset output of the flip-flop 52 to one of the inputs of the AND gate 54 prevents the arrival of a pulse at the set input of the flip-flop 52 at a moment when a pulse is applied to the reset input of the flip-flop 52. The synchronized code pulse sets the flip-flops 50 and 52, thus preparing the synchronization sub-unit 45 for the arrival of the next code pulse.

In the course of operation of the synchronization sub-unit 45, there may occur a partial coincidence in time of the code pulse and the synchronizing clock pulse. This may result in an "inadequate" pulse 58 (FIG. 5i) at the output of the AND gate 54, i.e. a pulse of an insufficient duration or amplitude. In such a case, the buffer flip-flop 52 may remain in the zero state until another successive synchronizing clock pulse is applied to the input of the AND gate 54. As at a moment of the arrival of the next synchronizing clock pulse, the state of the flip-flop cannot be changed, at the output of the AND gate 54 there appears a second ("adequate") pulse 59 (FIG. 6i) which sets the flip-flop 52 (FIG. 3). At a moment of the arrival of the next synchronizing clock pulse (FIG. 5e), at the output of the gate 56, there is formed a synchronized code pulse (FIG. 5l) which is applied to the output 17 of the synchronization unit 3 and simultaneously resets the flip-flops 50 and 52.

Synchronized code pulses corresponding to a negative increment of temperature are formed in a similar manner at the output of the gate 57 of the synchronization sub-unit 46. These pulses are applied to the output 18 of the synchronization unit 3.

Thus, the coincidence in time of pulses formed at the output of the gates 56 and 57 with those applied from the output of the gate 49 of the pulse distribution sub-unit 44 enables division in time of synchronized clock pulses and synchronized code pulses.

In order to ensure reliable operation of the synchronization unit 3, it is necessary that the repetition frequency $f_2$ of the synchronizing clock pulses should be double or treble the maximum repetition frequency $f_{3\ max}$ of the code pulses arriving from the output of the converter 1 (FIG. 1, i.e.

$$f_2 \geq 3 f_{3\ max} \tag{3}$$

Hence, the pulse frequency at the output of the generator 2 must be $$f_0 = 2 f_2 \geq 6 f_{3\ max.} \tag{4}$$

The synchronized code pulses from the outputs of the gates 56 and 57 of the synchronization unit 3 are respectively applied to the subtract and add inputs of the reversible counter 4 and the threshold counter 5.

As the reversible counter 4 is blocked by the flip-flop 10, the content of the reversible counter remains equal to the value $C_o$, despite the fact that the code pulses keep arriving at the counter's inputs. Each time, the temperature increment on the portions O-A and A-B (FIG. 6a) of the cooling curve each time when the temperature increment is equal to $\pm\epsilon_o$, there appear pulses at the overflow outputs of the threshold counter 5 (FIG. 1), which reset the time interval counter 7. Since the time intervals between initial settings of the time interval counter 7 are shorter than $\tau_o$, no pulses are formed at the overflow output of the time interval counter 7 (FIG. 1) on the portions O-A (FIG. 6a) and A-B.

Figures 6A, 6B, 6C, 6D:
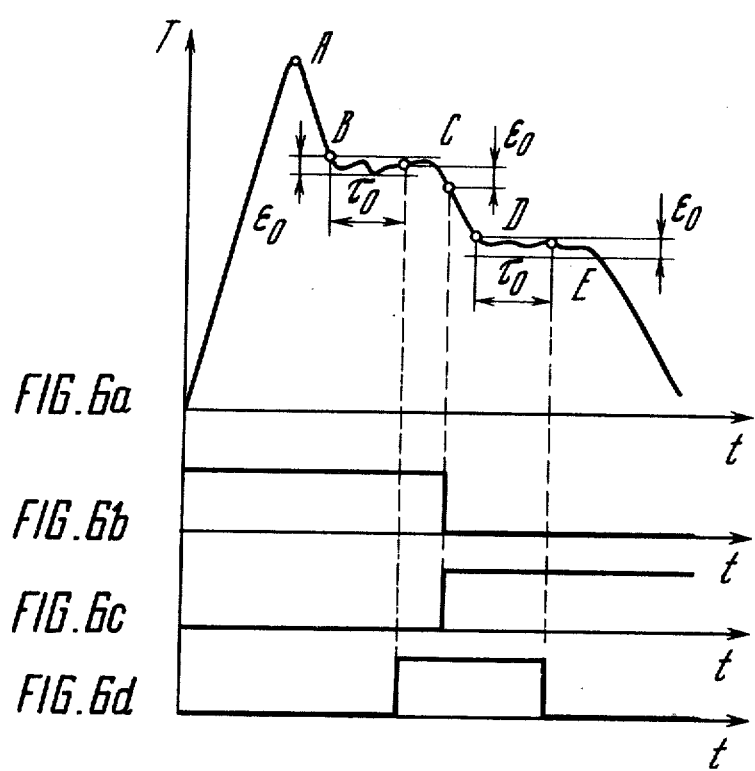
FIGS. 6a,b,c,d, show, respectively, a molten iron cooling curve of and time plots illustrating operation of the code selection unit, NOT element, and flip-flop, according to the invention.

At the point B (FIG. 6a) the temperature of the metal becomes equal to the liquidus temperature $T_e$ and the metal begins to crystallize. The portion B-C corresponds to the liquidus temperature arrest. As on this portion changes in the temperature of the metal do not exceed the value $\pm\epsilon_o$, no pulses are formed at the overflow outputs of the threshold counter 5 (FIG. 1) and the time interval counter 7 is not reset. As a result, after the period of time $\tau_o$ elapsed since the last resetting of the time interval counter 7, at the overflow output of the counter 7 there is formed a pulse which is applied to the inputs of the gates 8 and 9. Since the gate 8 is driven into conduction by the enabling potential (FIG. 6b) from the output of the code selection unit 6 (FIG. 1), and the gate 9 is rendered non-conducting by the disable potential (FIG. 6c) applied from the output of the NOT element 11, the overflow pulse of the time interval counter 7 sets passing through the gate 8 and the flip-flop 10 (FIG. 6d). Simultaneously, the reversible counter 4 (FIG. 1) is driven into conduction and starts counting code pulses. On the portion B–C (FIG. 6a), the state of the reversible counter 4 (FIG. 1) may be changed by a value not exceeding $\pm\epsilon_o$ relative to $C_o$ and therefore, the enable potential remains at the output 20 of the code selection unit 6. If on the portion B–C (FIG. 6a) there is formed another pulse at the overflow output of the time interval counter 7 (FIG. 1), i.e. if the duration of the liquidus temperature arrest is too long, the flip-flop 10 remains set, which rules out the next blocking of the reversible counter 4 at the temperature $T_1$.

On the portion C–D (FIG. 6a) the temperature of the metal changes from the liquidus temperature $T_1$ to the solidus temperature $T_s$. On this portion, the threshold counter 5 (FIG. 1) again resets the time interval counter 7 thus preventing it from overflowing. The code pulses change the content of the reversible counter 4. As soon as in the reversible counter 4 there is set a value differing from $C_o$ by a value exceeding $\epsilon_o$, a disable potential (FIG. 6b) is formed at the output 20 of the code selection unit 6. The gate 8 (FIG. 1) is blocked, and the signal (FIG. 6c) inverted by the NOT element 11 makes the gate 9 ready for passing another pulse.

At the point D, the temperature of the metal is equal to the solidus temperature $T_s$, and a second temperature arrest occurs on the cooling curve D–E. As the change in the temperature of metal does not exceed $\epsilon_o$, the threshold counter 5 does not reset the time interval counter 7, and after the period of time $\tau_o$ a pulse appears at the output of the time interval counter 7. Passing through the open gate 9, this pulse resets the flip-flop 10 (FIG. 6d). As a result, the signal from the "1" output of the flip-flop 10 (FIG. 1) again blocks the reversible counter 4. Thus the reversible counter 4 counts code pulses only on the portion C–D (FIG. 6a) and, therefore, its content at the moment of blocking is:

$$C_E = C_o + K(T_i - T_s) \tag{5}$$

where K is a proportionality factor.

The information output of the reversible counter 4 (FIG. 1) may be directly connected to a control computer wherein there is entered information on the carbon equivalent in the molten iron. This information may be transmitted to a digital display unit for the attending personnel.

The proposed digital device for checking the carbon equivalent in molten iron ensures a higher accuracy in determining the carbon equivalent, as compared with the known device.

The employment of simple functional computing units accounts for a high reliability, low cost and small dimensions of the device. The device can operate without any maintenance over prolonged periods of time.

In combination with any conventional measuring device, the proposed device may function as a digit transducer of the carbon equivalent in molten iron in a closed-loop control system for controlling iron melting processes with the use of a computer.

What is claimed is:

1. A digital device for checking the carbon equivalent in molten iron, comprising:
   a converter, which converts the actual temperature of a metal to a digital pulse code, having an input, whereto there is applied a signal carrying information on the actual temperature of the metal;
   a first output for code pulses corresponding to a positive increment of temperature;
   a second output for code pulses corresponding to a negative increment of temperature;
   a clock pulse generator having an output;
   a synchronization unit for time distribution of code and clock pulses, having;
   a first input connected to the first output of said converter which converts the actual temperature of the metal to a digital pulse code;
   a second input connected to the second output of said converter which converts the actual temperature of the metal to a digital pulse code;
   a third input connected to said output of said clock pulse generator,
   a first output for synchronized code pulses corresponding to a positive increment of temperature;
   a second output for synchronized code pulses corresponding to a negative increment of temperature, and a third output for synchronized clock pulses;
   a reversible counter for obtaining a parallel code of the carbon equivalent, having an add input connected to said synchronization unit;
   a subtract input connected to said first output of said synchronization unit;
   a count suppression input, and digit outputs;
   a threshold counter for pulse formation when a predetermined increment of the temperature information signal takes place, having an add input connected to said second output of said synchronization unit;
   a subtract input connected to said first output of said synchronization unit, and overflow outputs;
   a time interval counter for selection of time intervals when predetermined increments of the temperature information signal takes place, having a count input connected to said synchronized clock pulse output of said synchronization unit, reset inputs connected to said overflow outputs of said threshold counter, and an overflow output;
   a code selection unit for effecting signal formation when the metal temperature is reduced to a pre-set value with respect to the liquidus temperature, having inputs connected to said digit outputs of said reversible counter, and an output;
   a flip-flop, having a set input and a reset input, and an output connected to said count suppression input of said reversible counter;
   a NOT element, having an input connected to said output of said code selection unit, and an output;
   a first gate, having an input connected to said overflow output of said time interval counter,
   a control input connected to said output of said code selection unit; and
   an output connected to said set input of said flip-flop; and
   a second gate, having an input connected to said overflow output of said time interval counter;
   a control input connected to said output of said NOT element, and an output connected to said reset input of said flip-flop.

* * * * *